United States Patent
Garcia-Rubio et al.

(10) Patent No.: US 6,330,058 B1
(45) Date of Patent: Dec. 11, 2001

(54) SPECTROPHOTOMETRIC METHOD AND APPARATUS FOR BLOOD TYPING

(75) Inventors: Luis Humberto Garcia-Rubio, Temple Terrace; Smita Narayanan, Tampa; German Leparc, Tampa; Robert Potter, Tampa, all of FL (US); Sharyn Orton, Rockville, MD (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/548,569

(22) Filed: Apr. 13, 2000

Related U.S. Application Data

(60) Provisional application No. 60/129,270, filed on Apr. 14, 1999.

(51) Int. Cl.[7] .......................... G01N 33/48; G01N 33/53
(52) U.S. Cl. .......................... 356/39; 435/7.24; 435/7.25
(58) Field of Search .................. 356/39; 435/7.24, 435/7.25

(56) References Cited

U.S. PATENT DOCUMENTS

| | | |
|---|---|---|
| 4,079,393 | 3/1978 | Al Marachy et al. . |
| 4,213,764 | 7/1980 | O'Connor . |
| 4,223,680 | 9/1980 | Jöbsis . |
| 4,281,645 | 8/1981 | Jöbsis . |
| 4,446,239 | 5/1984 | Tsuji et al. . |
| 4,655,225 | 4/1987 | Dähne et al. . |
| 4,713,348 | 12/1987 | Ullman . |
| 4,805,623 | 2/1989 | Jöbsis . |
| 4,851,210 | 7/1989 | Hewett . |
| 4,988,630 | 1/1991 | Chen et al. . |
| 5,110,726 | 5/1992 | Ogden . |
| 5,180,661 | 1/1993 | Brubaker . |
| 5,197,470 | 3/1993 | Helfer et al. . |
| 5,259,382 | 11/1993 | Kronberg . |
| 5,261,410 | 11/1993 | Alfano et al. . |
| 5,325,295 | 6/1994 | Fratantoni et al. . |
| 5,336,597 | 8/1994 | McMillan . |
| 5,341,805 | 8/1994 | Stavridi et al. . |
| 5,377,674 | 1/1995 | Kuestner . |
| 5,674,699 | * 10/1997 | Saunders et al. .................. 435/7.93 |

* cited by examiner

Primary Examiner—Frank G. Font
Assistant Examiner—Roy M. Punnoose
(74) Attorney, Agent, or Firm—Allen, Dyer, Doppelt, Milbrath & Gilchrist, P.A.

(57) ABSTRACT

A method and apparatus for characterizing the type of a blood sample are provided wherein an optical density spectrum of the sample is collected over a predetermined wavelength range. A reference optical density spectrum is collected over a predetermined wavelength range for a portion of the blood sample diluted in saline. Another portion of the blood sample is then mixed with an antibody corresponding to a known blood type (e.g., anti-A, anti-B, anti-D antibody). The optical density spectrum is then collected over a predetermined wavelength range for blood diluted with saline and each antibody in saline. The slopes are then calculated over a predetermined wavelength range for each spectrum. A numerical indicator of agglutination is then calculated by dividing the slope of each antibody-treated sample by the slope of the sample in saline. The resulting number is multiplied by 100. The agglutination index (AI) is arrived at by subtracting this number from 100 so that the magnitude of the AI is a reflection of the degree of agglutination of the sample. A high index value indicates large agglutination (i.e., strong interaction with antibody). Blood type is determined by comparing the AI to a predetermined empirical cutoff value. Typically cutoff values greater than 17 indicate type-specific interaction (type AB samples yield AI values over 17 with both anti-A and anti-B antibodies, while type O samples yield AI values less than 17 with both anti-A and anti-B antibodies).

1 Claim, 11 Drawing Sheets

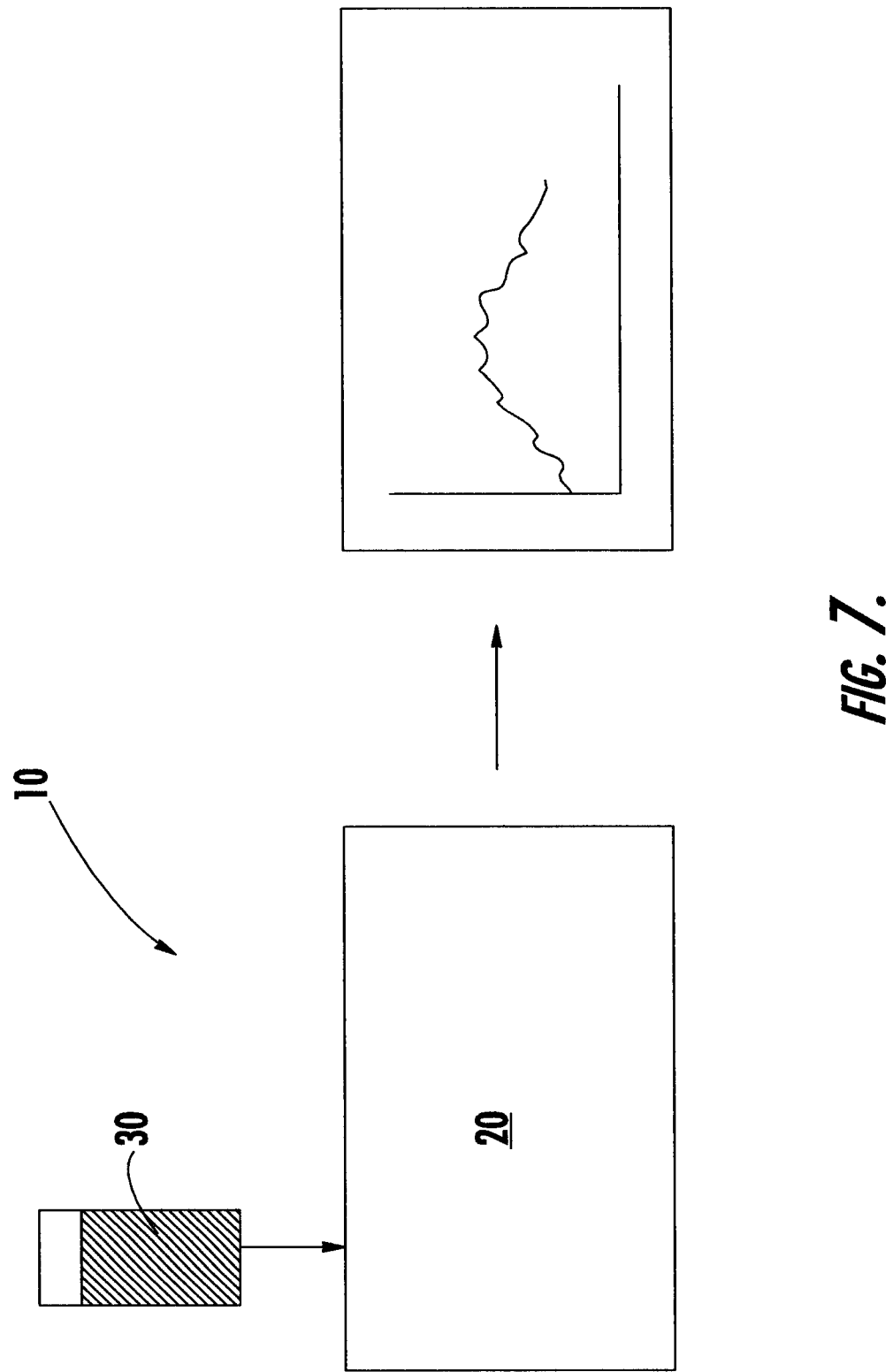

SPECTROPHOTOMETRIC METHOD AND APPARATUS FOR BLOOD TYPING

This application claims benefit of provisional No. 60/129,270 filed Apr. 14, 1999. +gi

GOVERNMENT SUPPORT

This invention was made with U.S. Government support under Grant RII-850756 from the National Science Foundation. The Government has certain rights in this invention.

BACKGROUND OF THE INVENTION

1. Field of the Invention

The present invention relates to the characterization of blood types, and, more particularly, to a spectrophotometric apparatus and method of blood typing.

2. Description of Related Art

Blood typing is the most commonly used test in blood centers and transfusion medicine (Beutler et al., 1995). Manual blood typing methods are time-consuming, require special skills, and are prone to errors. Automated systems involve expensive and complex instrumentation. In addition, these methods do not lend themselves to a quantitative interpretation of the antibody-induced aggregation process. Consequently, there has been ongoing interest in developing alternative methods for blood typing. This had led us to examine the utility of a simple and easily automated approach, namely, multiwavelength ultraviolet/visible spectroscopic analysis as a potential quantitative blood typing procedure.

The basis for currently known blood typing methods is the examination of blood samples for aggregation in the presence of agglutinating antibodies (Walker et al., 1990; Gane et al., 1987). At present, the most sophisticated automated blood typing procedure uses image analysis measurements of incubated mixtures of test and reagent samples in optically clear reaction chambers (Olympus, 1993). A special camera records the light transmission pattern throughout the image to distinguish between a positive and negative agglutination test. Manual approaches employed in smaller clinical settings use tube testing that relies on the technician's subjective visual recognition of aggregates. An alternate multistep test uses bromelain-treated erythrocytes adhering to microtiter plates; typing is accomplished via analysis of coagglutination with erythrocytes of unknown sera following centrifugation and evaluation of optical image patterns (Muller et al., 1981).

One limitation of the currently employed technology is a lack of on-line capability for the characterization of blood components, as well as a lack of portable instrumentation capable of detecting, counting, and classifying specific blood components. The problem of portable instrumentation and suitable methods of analysis and diagnosis is particularly relevant to the medical industry, where the need for rapid analysis and diagnosis often involves life-threatening situations. Although the analytical instrumentation used in medical and clinical laboratories has improved considerably over the past decade, there are still no suitable techniques capable of detecting, classifying, and counting on-line critical cell populations and/or pathogens in blood and other bodily fluids. Typically the particles of interest have sizes ranging between 0.5 and 20 $\mu$m, and, in many instances, are present in fairly dilute concentrations.

As is known from spectroscopy theory, a measure of the absorption of a solution is the extinction coefficient, which also provides a measure of the turbidity and transmission properties of a sample. Spectra in the visible region of the electromagnetic spectrum reflect the presence of certain metal ions, complexes, and molecules with extensive conjugated aromatic structures. In the near-uv region small conjugated ring systems affect absorption properties. However, suspensions of very large particles are powerful scatterers of radiation, and in the case of microorganisms, the light scattering effect is sufficiently strong to mask or distort absorption effects. It is therefore known to use uv/vis spectroscopy to monitor purity, concentration, and reaction rates of such large particles.

Many attempts have been made to estimate the particle size distribution (PSD) and the chemical composition of suspended particles using optical spectral extinction (transmission) measurements. However, previously used techniques require that either the form of the PSD be known a priori or that the shape of the PSD be assumed. One of the present inventors has applied standard regularization techniques to the solution of the transmission equation and has demonstrated correct PSDs of a large variety of polymer lattices, protein aggregates, silicon dioxide particles, and microorganisms.

It is also possible to use the complementary information available from simultaneous absorption and light scattering measurements at multiple angles for the characterization of the composition and molecular weight of macromolecules (Garcia-Rubio, 1993; and "Multiangle, Multiwavelength Particle Characterization System and Method," U.S. patent application Ser. No. 08/489,940, filed Jun. 13, 1995, now abandoned, and continuation application thereto U.S. patent application Ser. No. 08/780,828, filed Jan. 10, 1997, now U.S. Pat. No. 5,808,738 the disclosures of which are incorporated herein by reference).

SUMMARY OF THE INVENTION

It is therefore an object of the present invention to provide a spectroscopic technique for the characterization and differentiation of blood types.

It is another object to provide on-line instrumentation capable of rapid spectrophotometric blood typing.

It is an additional object to provide such instrumentation having at least 2 nanometer resolution.

These and other objects are addressed by the apparatus and method of the present invention for a method for determining the type of a blood sample. The method takes advantage of the fact that a suspension of cells both absorb and scatter light (Anderson et al., 1967). The results of these combined effects yield the optical density or transmission. Typically large biological particles such as cells exhibit scattering throughout the uv/visible range and absorption generally below 800 nm due to their specific chromophoric components (Kerker, 1969). In the past uv/vis spectroscopy has been used extensively to examine specific components of blood. These have typically been analyzed in reference to calibrations carried out with internal or external standards. An example of this is hemoglobin measurement, which has been determined using optical density measurements of erythrocytes, where these values are calibrated against hemoglobin obtained from erythrocytes following lysis (Horecker, 1943).

Simple, rapid, inexpensive, and nondestructive direct interpretation of the size and composition information contained in a uv/vis spectrum have not been fully exploited. This has primarily been due to the difficulty in quantitatively interpreting nonlinear scattering effects combined with an equally confounding hypochromic effect arising from the dense packing of strongly absorbing species such as hemoglobin in erythrocytes (Horecker, 1943; Horecker and Brackett, 1944). For these reasons, uv/visible spectroscopy has been mainly used to obtain qualitative differences between complex mixtures or has required interpretations based on external calibrations or standards as described above. While certain scattering theories have been developed that relate the number of particles, size of particles, and number and types of absorbing species to the actual optical density spectrum, e.g., Mie scattering theory (Brandolin et al., 1991), solutions for such equations require knowledge of the refractive index of the components as well as either their absorption or scattering characteristics (Garcia-Rubio, 1992). Given the complexity of a solution such as whole blood, this can be a daunting task but one that nevertheless merits effort.

The method of the present invention comprises the steps of collecting a reference optical density spectrum over a predetermined wavelength range for a portion of the blood sample diluted in saline. Another portion of the blood sample is then mixed with an antibody corresponding to a known blood type (e.g., anti-A, anti-B, anti-D antibody). The optical density spectrum is then collected over a predetermined wavelength range for blood diluted with saline and each antibody in saline. The slopes are then calculated over a predetermined wavelength range for each spectrum. A numerical indicator of agglutination is then calculated by dividing the slope of each antibody-treated sample by the slope of the sample in saline. The resulting number is multiplied by 100. The agglutination index (AI) is arrived at by subtracting this number from 100 so that the magnitude of the AI is a reflection of the degree of agglutination of the sample. A high index value indicates a large agglutination (i.e., a strong interaction with antibody). Blood type is determined by comparing the AI to a predetermined empirical cutoff value. Typically cutoff values greater than 17 indicate type-specific interaction (type AB samples yield AI values over 17 with both anti-A and anti-B antibodies, while type O samples yield AI values less than 17 with both anti-A and anti-B antibodies).

In the preferred embodiment of the method of the invention, the predetermined wavelength range comprises generally the ultraviolet-to-visible wavelength range, most preferably from 600 to 1000 nm. A portion of the spectral information that is easily accessible is used to develop a simplified blood typing test. By utilizing predominantly the light scattering component of the spectrum beyond 665 nm, which changes dramatically with aggregation, a numerical gauge of antibody-induced erythrocyte agglutination is calculated. The increasing interaction of type-specific antibodies with red blood cells leads to agglutination and is reflected by an increase in the agglutination index. The index is shown to be related by theory to changes in the size and number of aggregates. This typing system has the advantage of using simple, relatively inexpensive equipment, can indicate hemolysis in blood samples, and produces a reliable numerical agglutination index. The latter characteristic makes full automation and field applications of this blood typing process possible.

The apparatus of the present invention comprises means for performing the above-listed steps. In a particular embodiment, the spectrum collecting means comprises a spectrophotometer.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 7 is a block diagram of the system configuration.

DETAILED DESCRIPTION OF THE PREFERRED EMBODIMENTS

Figure 1A:
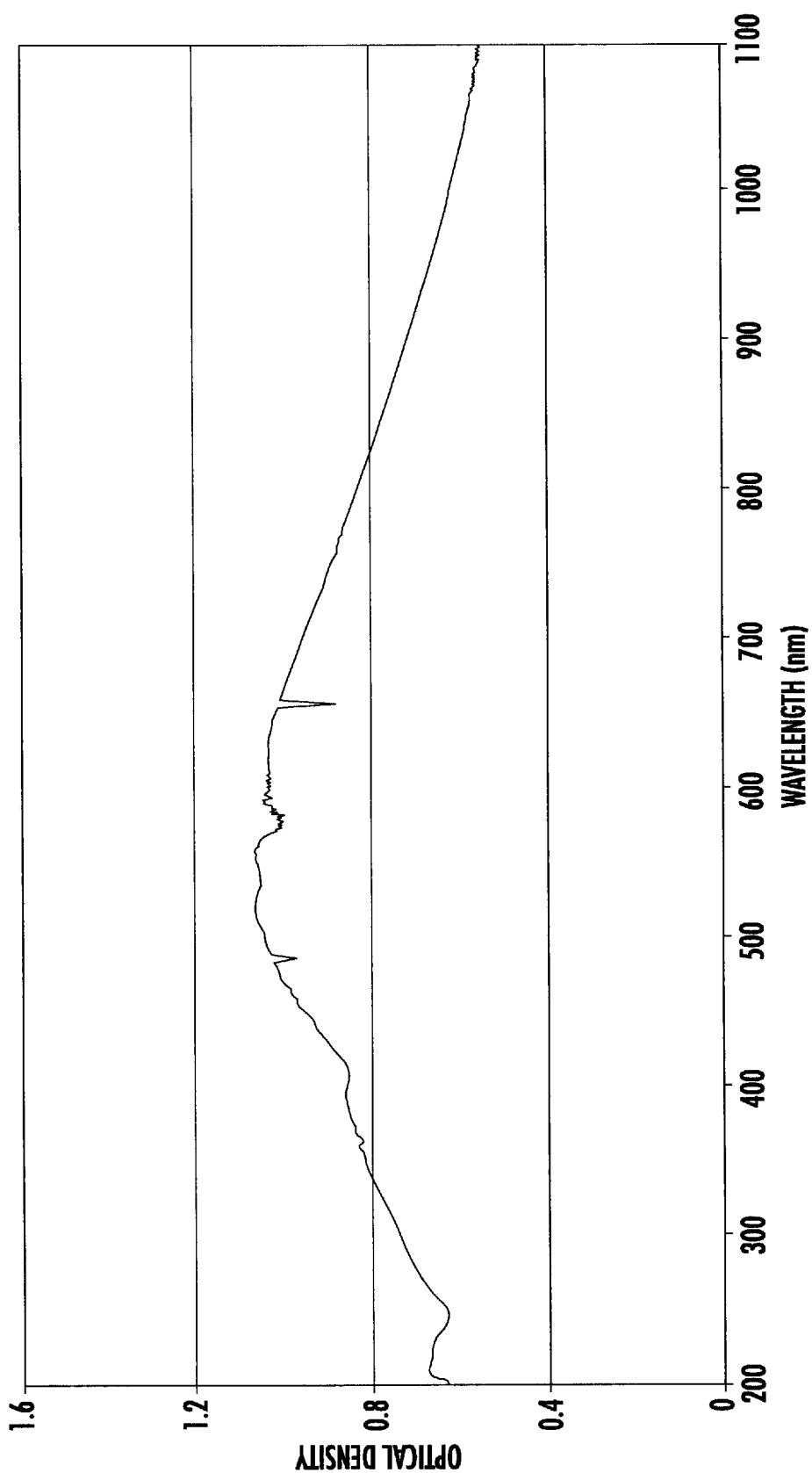
FIG. 1A plots an optical density spectrum of a dilute packed red cell suspension in saline. The peaks at 486 and 656 nm are instrumental artifacts.

A description of the preferred embodiments of the present invention will now be presented with reference to FIGS. 1–7.

THEORETICAL BACKGROUND AND DEVELOPMENT

Dilute Dispersions

The optical spectral extinction of a particle dispersion such as whole blood or a sample of blood components contains information that, in principle, can be used to estimate the particle size distribution (PSD) and the chemical composition of the suspended particles. A large number of techniques for the estimation of the PSD from transmission spectra have been reported (van de Hulst, 1957, Kerker, 1962; Rousseau, 1984). Unfortunately, most of these techniques require that either the form of the PSD be known a priori, or that the shape of the PSD be assumed (Zollars, 1980; Melik and Fogler, 1983). More recently, regularization techniques (Towmey, 1979; Golub, 1979; Tarantola, 1987), applied to the solution of the transmission equation (Elicabe and Garcia-Rubio, 1990), have been demonstrated to yield the correct particle size distribution of a large variety of polymer lattices (Brandolin and Garcia-Rubio, 1991) and protein aggregates (Garcia-Rubio et al., 1993), $SiO_2$ particles (Chang et al., 1995), and microorganisms (Garcia-Rubio and Rose, unpublished). The present inventors have devised a technique for determining a discretized particle size distribution from transmission spectra. The equations providing the theoretical framework are developed from a relation between the transmission as a function of wavelength $\tau(\lambda_0)$ and the normalized particle size distribution $f(D)$:

$$\tau(\lambda_0) = N_p(\pi/4)\int_0^\infty Q(\lambda_0, D)D^2 f(D)\,dD, \quad (1)$$

where D is the effective particle diameter, $Q(\lambda_0,D)$ corresponds to the Mie scattering coefficient, and $N_p$ is the number of particles per unit volume. Equation (1) can be written in matrix form by discretizing the integral with an appropriate quadrature approximation (Elicabe and Garcia-Rubio, 1990):

$$\tau = Af + \epsilon, \quad (2)$$

where $\epsilon$ represents both experimental errors and errors due to the model and the discretization procedure (Elicabe and Garcia-Rubio, 1990). The regularized solution to Eq. (2) is given by:

$$f(\gamma) = (A^TA + \gamma H)^{-1}A^T\tau, \quad (3)$$

where H is a covariance matrix that essentially adaptively filters the experimental and the approximation errors ($\epsilon$), and $\gamma$ is the regularization parameter estimated using the generalized cross-validation technique (Golub et al., 1979). This technique requires the minimization of the following objective function with respect to $\gamma$ (Golub et al., 1979):

$$V(\gamma) = m\|[I-A(A^TA+\gamma H)^{-1}]\tau\|^2/Tr\{[I-A(A^TA+\gamma H)^{31\,1}]A^T\}^2 \quad (4)$$

A simultaneous application of Eqs. (3) and (4) to the measured transmission spectra yields the discretized particle size distribution. Using the appropriate optical properties of the materials, the solution to Eqs. (3) and (4) will yield the relative proportions of particles with different chemical composition present in the sample. Note that all the parameters required for the calculation of particle size distribution are obtained from the data. The scattering corrected spectra can also be used for composition analysis and/or to fingerprint the absorption characteristics of the particles.

Blood Typing Apparatus and Method Using Whole Blood

The apparatus 10 and method of using same for determining the type of a blood sample are depicted in FIG. 7. This embodiment can be performed with portable equipment, and hence can serve as a rapid, on-line technique.

In the particular embodiment of the method to be treated herein, packed red blood cells are used for the blood samples. In an alternate embodiment, whole blood may be used. Dilution is required prior to quantitative spectrophotometric measurements to reach a linear range of the spectrophotometer 20, which will be discussed further in the following.

Using a spectrophotometer 20, such as a Hewlett Packard 8453 Diode Array Spectrophotometer, a transmission spectrum of the sample 30 is collected over a predetermined wavelength range. In the preferred embodiment the predetermined wavelength range comprises generally the ultraviolet-to-visible (uv/vis) wavelength range.

BLOOD TYPING

Whole blood of known blood type, no more than 24 hours old, was either analyzed directly or a sample of 10–20 ml of whole blood was centrifuged for 20 min at 1720×g, yielding packed red blood cells and a buffy coat. The plasma above the packed cells was carefully removed with a pipette, and the packed cells were then used immediately for further analysis.

Owing to the optically dense nature of packed cells, considerable dilution is required to obtain reliable data from quantitative spectrophotometric measurements. Both whole blood and packed red blood cells were diluted substantially before spectroscopy, in order to obtain spectra with absorbances of 1.2 or less. Whole blood was diluted 1:8 to a solution and the packed cells 1:16 with phosphate buffered saline (0.1 50M sodium chloride, 0 006M sodium biphosphate, and 0 002M potassium phosphate pH 7.0–7.2; Criterion Sciences) to achieve a final concentration of approximately 4000 red blood cells per microliter. In order to generate spectra representing only the blood components, background spectra of saline or diluted antibody in saline were taken and used as described below.

All spectroscopic measurements were made on a Hewlett Packard 8453 Diode Array Spectrophotometer 20. Optical density (OD) spectra were taken over an integration time of 15 sec, 10 spectra being taken every 1 sec, yielding an average spectrum of 150 separate measurements.

Generation of Blood Control Spectrum

An ultraviolet/visible (uv/vis) spectrum of blood (190–1100 nm) diluted in saline served as a control to which antibody-blood interaction spectra could be subsequently compared.

Saline Background. A uv-vis spectrum of saline was obtained which was subtracted from all subsequent readings of packed cells and commercial red cells.

Whole Blood/Packed Red Cells Control Spectrum. A diluted whole blood sample of 100 μl was added to 100 μl of saline. This mixture was incubated for 1 min. A portion (25 μl) of this solution was then delivered into a cuvette containing 2.5 ml of saline and its contents mixed by inversion. The uv/vis spectrum of the sample was measured and the background automatically subtracted. This analysis served as the unmodified whole blood control spectrum (i.e., in the absence of antibody). This procedure was also followed to obtain the control spectrum for samples of packed red cells and commercial red cells.

Analysis of Blood-Antibody Interaction Anti-A, Anti-B, and Anti-D monoclonal antibodies were obtained either from Gamma Biologicals Inc. (Houston, TX) or Ortho Diagnostics (Raritan, NJ). Anti-A and Anti-B antibodies were diluted 1:16 and 1:8, with saline, respectively, for all agglutination analyses. Anti-D solutions were used as supplied. Preliminary experiments were carried out in each case, in order to determine the amount of antibody that led to visual agglutination using a manual method.

Test Sample. A sample of 100 µl of diluted antibody was added to 100 µl of diluted whole blood. This mixture was incubated for 1 min and 25 µl was delivered to a cuvette containing 2.5 ml of saline. The sample was mixed by inversion and the uv/vi spectrum was measured. The antibody background (consisting of antibody diluted in saline) was subtracted from the test sample reading. For experiments in which the antibody-blood interaction was monitored over time, the incubation intervals were increased from 1 min to 5, 10, 20, or 30 min. Incubated samples were analyzed spectrophotometrically to monitor change in aggregation. In most cases data was normalized, i.e., all the spectrometric absorbances were divided by the absorbance value at 460 nm to eliminate concentration differences between the samples.

Reverse grouping. Whole plasma isolated from whole blood was used instead of antiserum to study aggregation effects as above. The plasma was not diluted.

The sensitivity of this technique was determined by mixing reagent red blood cells (Immucor, Norcross, GA) of blood type A with anti-A and anti-B of varying concentrations, namely, 1:3–1:1536-fold dilutions in phosphate-buffered saline as described above.

Agglutination Index. Spectral slopes between 665 and 1000 nm were determined from spectra of blood-saline and blood-antibody treated samples. This wavelength range was within the linear portion of the spectrum. The standardized slopes were obtained by dividing the slope of the antibody-treated sample and the control (saline sample) by the control slope (saline sample), with the resulting number multiplied by 100. Hence the standardized saline slope is always 100 and the other slopes are multiples of it. The agglutination index is then obtained by subtracting the standardized slope of the antibody-treated sample from the standardized slope for the control.

agglutination index (AI)=100−(slope of antibody-treated sample)× 100/(slope of sample in saline)

Results

Figure 1B:
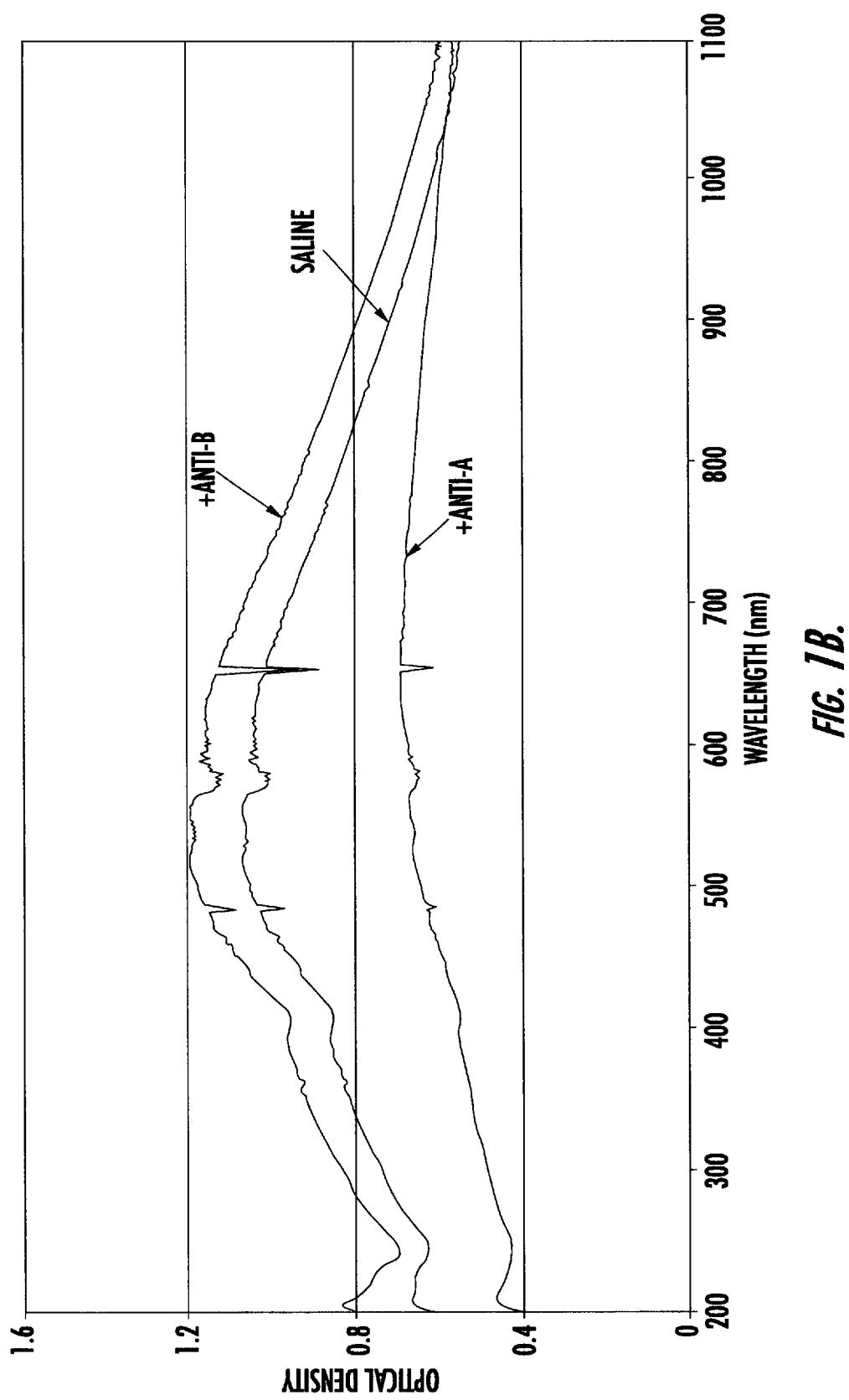
FIG. 1B plots an optical density spectrum of type A blood in the presence of anti-A and anti-B reagents. The differences between the saline sample and that in anti-B are predominantly due to slight differences in red blood cell concentration.
Figure 1C:
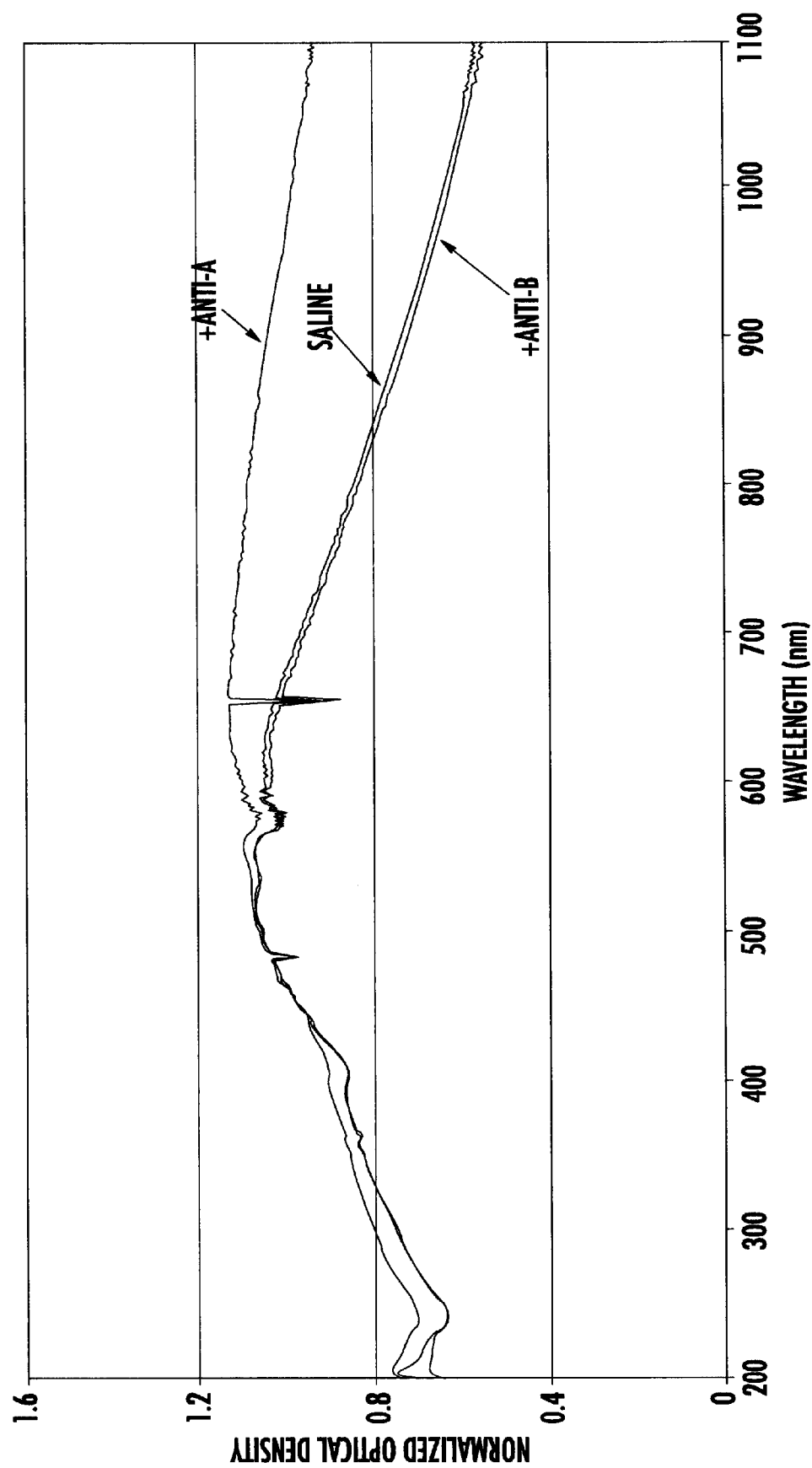
FIG. 1C plots an optical density spectrum of packed cells of type A blood in the presence of anti-A and anti-B reagents, normalized relative to the intensity at 460 nm. This amplifies changes in the spectrum that are independent of slight concentration differences that arise owing to dilution of the samples in saline.

A typical diluted spectrum of packed cells from blood suspended in saline is shown in FIG. 1A. Prominent forward scattering from the various blood cells is easily identified at wavelengths above 600 nm, where there is little to no absorbance from chromophores. Absorption components due mainly to the high concentration of hemoglobin in the red cells contribute to the broad peak observed between 460 and 540 nm. The spectral features appearing as sharp spikes at 486 and 656 nm are artifacts of the HP8453 diode array spectrophotometer and thus are not attributed to spectral characteristics of red cells. Addition and incubation of agglutinating antibody for as little as 1 min causes significant changes in the spectrum, as shown in FIG. 1B. There is a general flattening of the spectra and an overall loss of optical density. Addition of nonagglutinating antibody (also FIG. 1B) to an equivalent sample shows a slight increase in overall optical density but little to no change in spectral features. The differences in the spectra are most easily seen by normalizing the spectra at 460 nm (a general maximum for blood spectra and a wavelength outside the range where the AI is calculated). This is achieved by dividing the optical density value obtained at each wavelength by the value obtained at 460 nm. Thus all values at 460 nm are set equal to 1. This essentially moves the spectrum up or down (changes magnitude) but does not affect the features of the spectrum. FIG. 1C shows the same. This procedure allows a comparison of the related spectra independent of any small concentration differences that arise from making the separate dilutions of the concentrated blood samples that are necessary for analysis. This comparison clearly shows that the spectral patterns of the control saline sample and blood in the presence of nonagglutinating antibody are highly similar, while an equivalent sample in the presence of agglutinating antibodies shows a significant difference.

The spectral differences between the sample in saline and that in anti-A are predominantly due to changes in scattering attributed to changes in the size of particles with cell aggregation. This trend was consistently observed in all 9 samples of blood type A. As expected, the spectrum of the sample in the presence of anti-B, which does not react with cells carrying the type A antigen, is virtually unchanged.

Agglutination Index (AI). Since a more quantitative analysis of the results would make automation of the blood typing process easier, we used numerical information from the spectra to develop a reliable index of agglutination. By analyzing the slopes of the spectra for control versus antibody-treated blood samples above 665 nm, where there is no absorption and forward scattering is the main determinant of optical density, a numerical assessment of agglutination is obtained. Importantly, the index agrees with standard blood typing reactions, and the values obtained correlate to the type and binding characteristics of the antibody; i.e., the stronger agglutination reactions yield nation indexes (30–100), while nonagglutinating systems yield values less than 1 (Table 1a).

TABLE 1a

Agglutination Index: Red Blood Cells vs. Anti-A or B Reagent Antibody

| Sample # | Antibody | Blood Type* | Standardized Slope Slope/Saline Slope | Agglutination Index |
|---|---|---|---|---|
| #1 in saline | none | A positive | 100 | 0.00 |
| 1 | Anti-A | " | 68.1 | 31.9 |
| 2 | Anti-A | A positive | 52.9 | 47.1 |
| 3 | Anti-A | A negative | 37.1 | 62.9 |
| 4 | Anti-A | " | 12.5 | 87.5 |
| 5 | Anti-B | B positive | 47.1 | 52.9 |
| 6 | Anti-B | " | 34.5 | 65.5 |
| 7 | Anti-B | B positive | 49.3 | 50.7 |
| 8 | Anti-B | " | 42.9 | 57.1 |
| 9 | Anti-A | AB positive | 46.6 | 53.4 |
| 9 | Anti-B | AB positive | 78.8 | 21.2 |
| 10 | Anti-A | AB positive | 51.6 | 48.4 |
| 10 | Anti-B | AB positive | 82.1 | 17.9 |
| 11 | Anti-A | AB positive | 66.3 | 33.7 |
| 11 | Anti-B | AB positive | 78.5 | 21.5 |
| 12 | Anti-A | O positive | 99.4 | 0.6 |
| 12 | Anti-B | " | 103.0 | −3.0 |
| 13 | Anti-A | " | 99.5 | 0.5 |
| 13 | Anti-B | " | 102.8 | −2.8 |
| 14 | Anti-A | O negative | 105.7 | −5.7 |
| 14 | Anti-B | " | 105.8 | −5.3 |

*from certified blood banking procedures

Packed red blood cell samples of blood type B yielded similar results as those seen for type A in the presence of anti-B antibody but not in the presence of anti-A antibody, and this was reflected numerically by the AI. Samples of type A, type B, and type AB all show the consistent behavior of small AI (<1) for nonagglutinating systems and large AI (>17) for agglutinating systems. Blood type O, as expected, showed no reaction (i.e., any significant spectral changes) with either anti-A or anti-B. In accordance with the spectral findings, AIs calculated were 1 unit or less for all three samples, as opposed to the agglutinated reaction indices that ranged from 17 to 103 units for A, B, or AB type cells in the presence of anti-A or anti-B, respectively (Table 1a). Spectroscopic blood typing experiments were also performed to evaluate the ability of the AI to identify D-positive or D-negative cells. Analysis on a total of six samples yielded expected results; AIs obtained were high (42–74) for D-positive (Rh-positive) samples and low (1.2 to 3.9) for D-negative (Rh-negative) samples (Table 1b).

TABLE 1b

Red Blood Cells vs. Anti-D Reagent

| Sample # | Blood Type | Standardized Slope Slope/Saline Slope | Agglutination Index |
|---|---|---|---|
| 15 | A positive | 57.8 | 42.2 |
| 16 | " | 26.2 | 73.8 |
| 17 | " | 52.2 | 47.8 |
| 18 | A negative | 101.2 | -1.2 |
| 19 | " | 96.1 | 3.9 |
| 20 | O negative | 97.6 | 2.4 |

Three samples of reagent red blood cells were also typed and evaluated for an AI using our agglutination indices were obtained where expected, namely, A-type cells in A (>60) and B-type cells with anti-B (>60) (Table 1c).

TABLE 1c

Reagent Red Blood Cells: Groups A and B vs. Anti-A or B

| Sample # | Antibody | Blood Type | Standardized Slope Slope/Saline Slope | Agglutination Index |
|---|---|---|---|---|
| 21 | Anti-A | A | 37.1 | 62.9 |
| 22 | Anti-A | A | 11.3 | 88.7 |
| 23 | Anti-B | B | 38.2 | 61.8 |

Figure 2A:
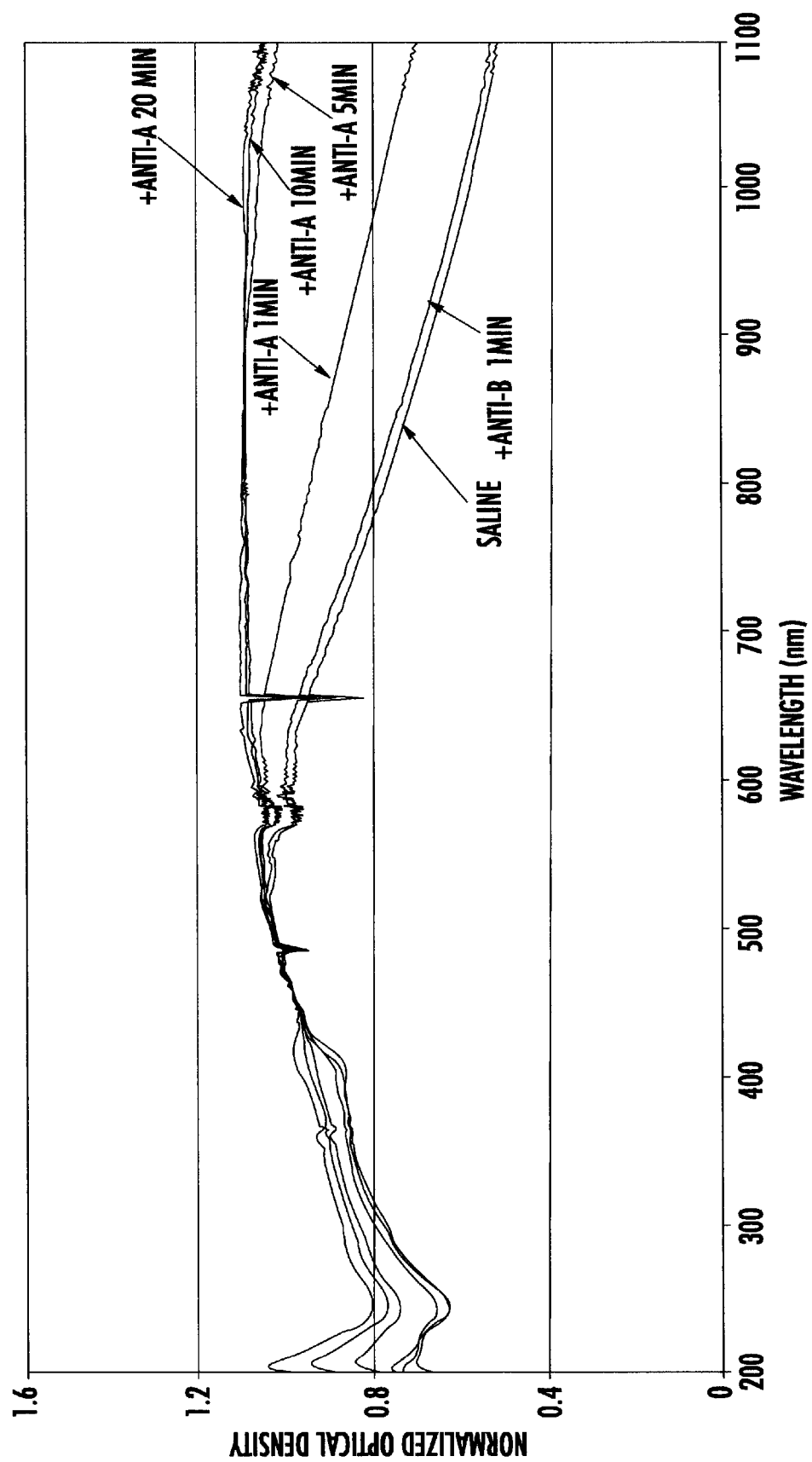
FIG. 2A plots a time study of optical density spectra of type A red blood cells with anti-A reagent (1–20 min incubation) normalized relative to the optical density at 460 nm. Spectroscopically agglutination is detectable at 1 min, although a dramatic increase is seen after 5 min, followed by a gradual increase in normalized optical density.
Figure 2B:
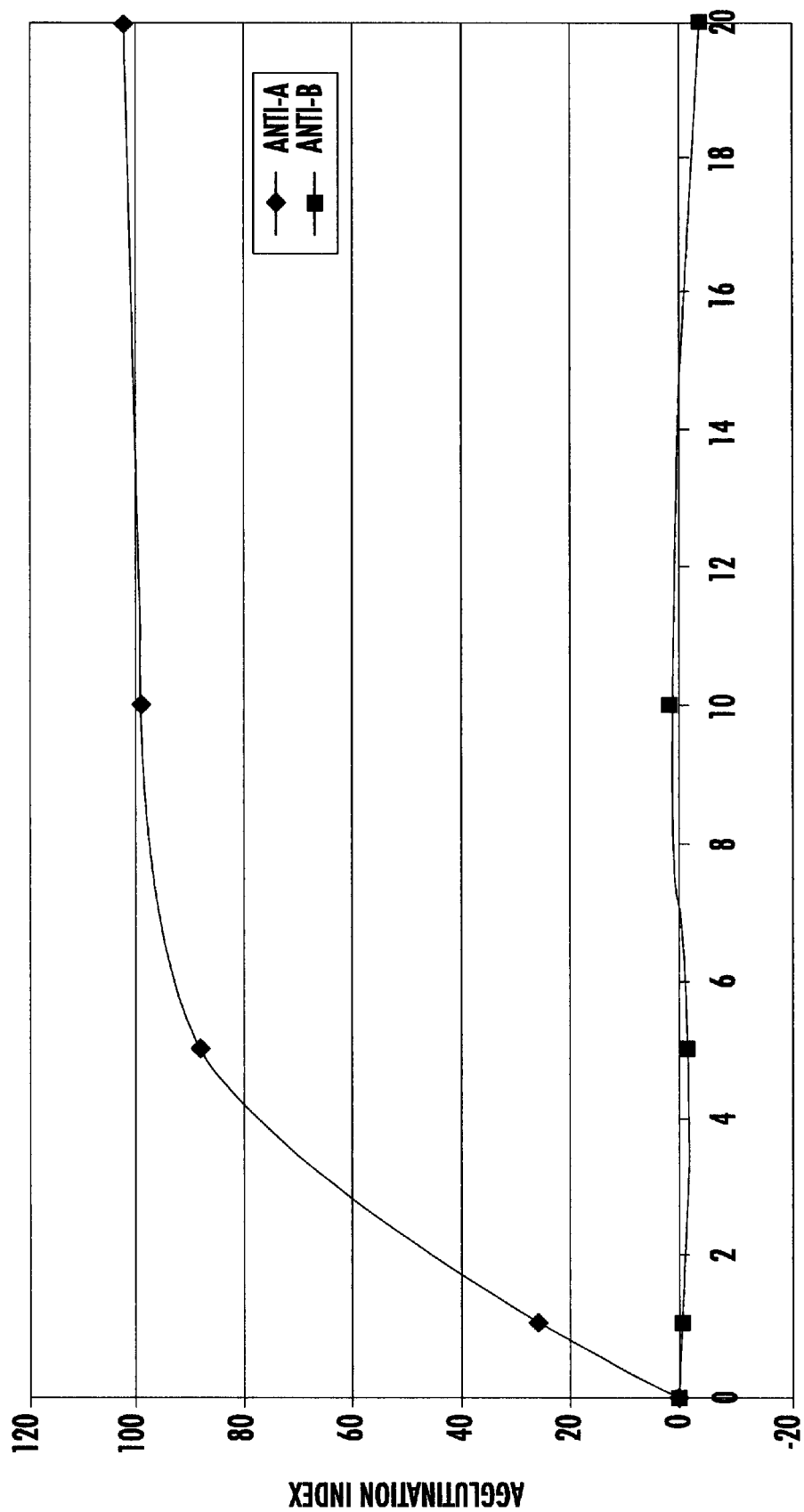
FIG. 2B plots the agglutination index versus incubation time of type A blood in the presence of anti-A and anti-B reagents. With anti-A reagent there is a dramatic increase in agglutination index until 5 min. The agglutination index with anti-B reagent shows little to no change.

FIG. 2A is a normalized analysis of blood type-A red cells in the presence of anti-A and anti-B over a 20-min incubation time. A consistent flattening of the spectra with greater time of incubation was noted. Visually, the agglutinated spectra did not change significantly after the fifth continued to flatten slightly until the last study at 20 min of incubation. These observations were further tested quantitatively. AIs were found to increase with time in the former case and to decrease in the latter, which is known to be a function of increasing and decreasing particle size of the aggregates, respectively (FIG. 2B). Higher values indicate a greater degree of antibody-red cell interaction, as corroborated by tube test results. The AI did not increase significantly after 5 min of incubation and was significant by 1 min, as used for most of the study

TABLE 2

Time Study of Blood Type A with Anti-A Reagent

| Sample | Antibody | Standardized Slope Slope/Saline Slope | Agglutination Index |
|---|---|---|---|
| Type A - 1 minute | Anti-A | 73.2 | 26.8 |
| Type A - 5 minutes | " | 12.2 | 87.8 |
| Type A - 10 minutes | " | 1.8 | 98.2 |
| Type A - 20 minutes | " | -2.6 | 102.6 |
| Type B | Anti-A | 101.5 | -1.5 |

Reverse grouping, a standard blood banking technique, used to confirm blood-typing results, was performed to test the viability of the new blood-typing system. Reagent red blood cells (Immucor, Norcross, Ga.), types A and B (Table 3), were analyzed for agglutination with both A type and B type plasma from donors. Standard normalization at 460 nm showed nonlinear differences in the intensities of all 3 spectra, not previously encountered, due presumably to the effects of added plasma on the shape of red cells and consequently on the spectra of red cells.

Figure 3:
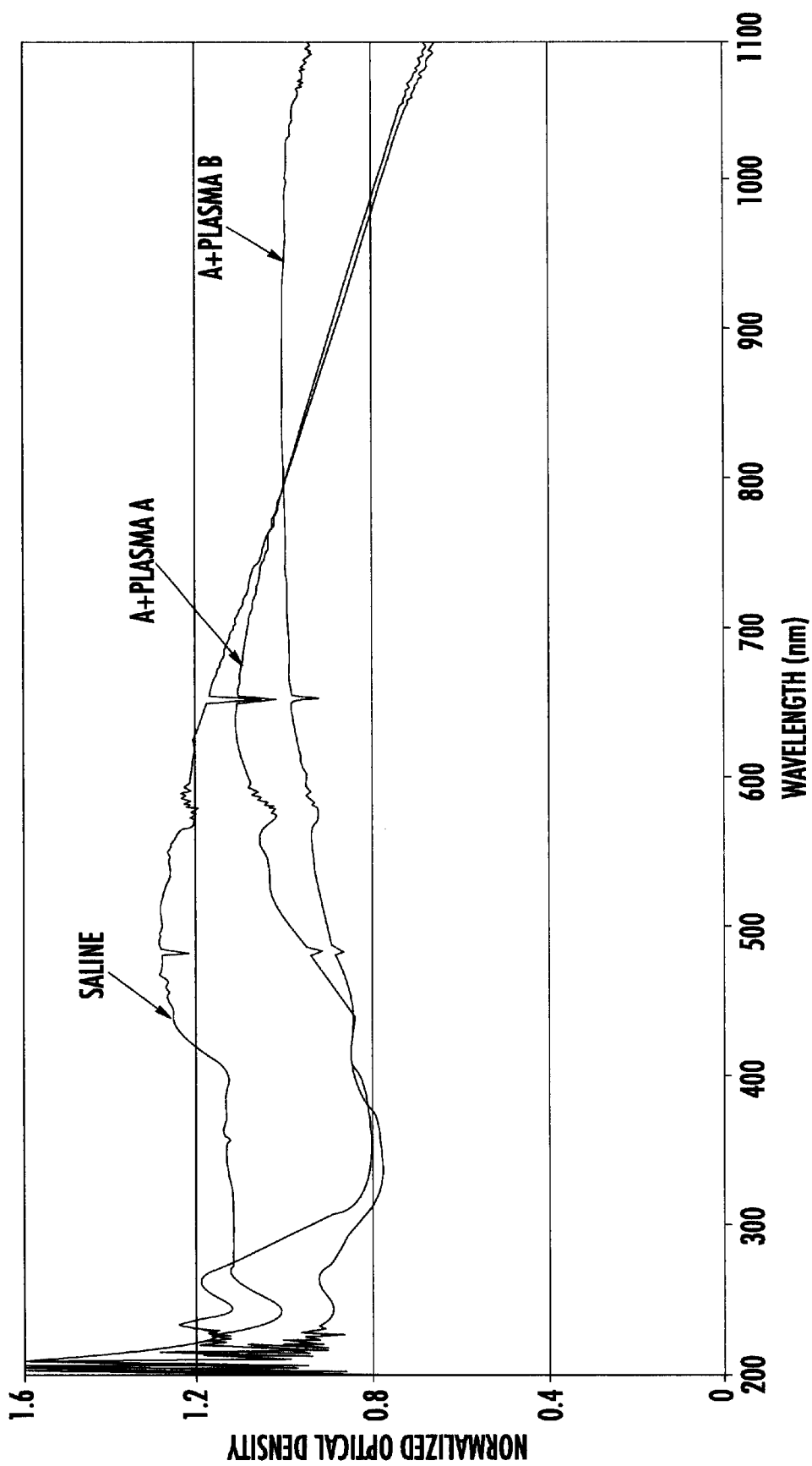
FIG. 3 plots a normalized optical density spectrum of blood type A in the presence of type A and B plasmas. The spectra were normalized relative to the OD at 800 nm instead of 460 nm to enhance differences in the slopes between 700 and 1000 nm.

Reverse grouping spectra were normalized at 800 instead of 665 nm, making it simpler to compare slopes visually (FIG. 3). This manipulation did not affect the AIs, since both control and reference spectra are normalized relative to the same wavelength. The slopes used to calculate the AI were taken from the most linear portion of the spectra, between 750 and 1000 nm. The indices of the blood-saline and blood with control plasma were similar in magnitude and spectral appearance, while that of blood in the presence of agglutinating plasma was markedly different, indicative of a strong agglutination reaction (FIG. 3). The same was carried out with group B reagent red blood cells with similar results (Table 3).

TABLE 3

Reverse Grouping: Types A and B vs. Plasma from A and B Donors

| Sample # | Antibody | Blood Type | Standardized Slope Slope/Saline Slope | Agglutination Index |
|---|---|---|---|---|
| 24 | Plasma A | A | 97.3 | 2.7 |
| 24 | Plasma B | " | -6.9 | 106.9 |
| 25 | Plasma A | B | 36.3 | 63.7 |
| 25 | Plasma B | " | 96.6 | 3.4 |

Figure 4A:
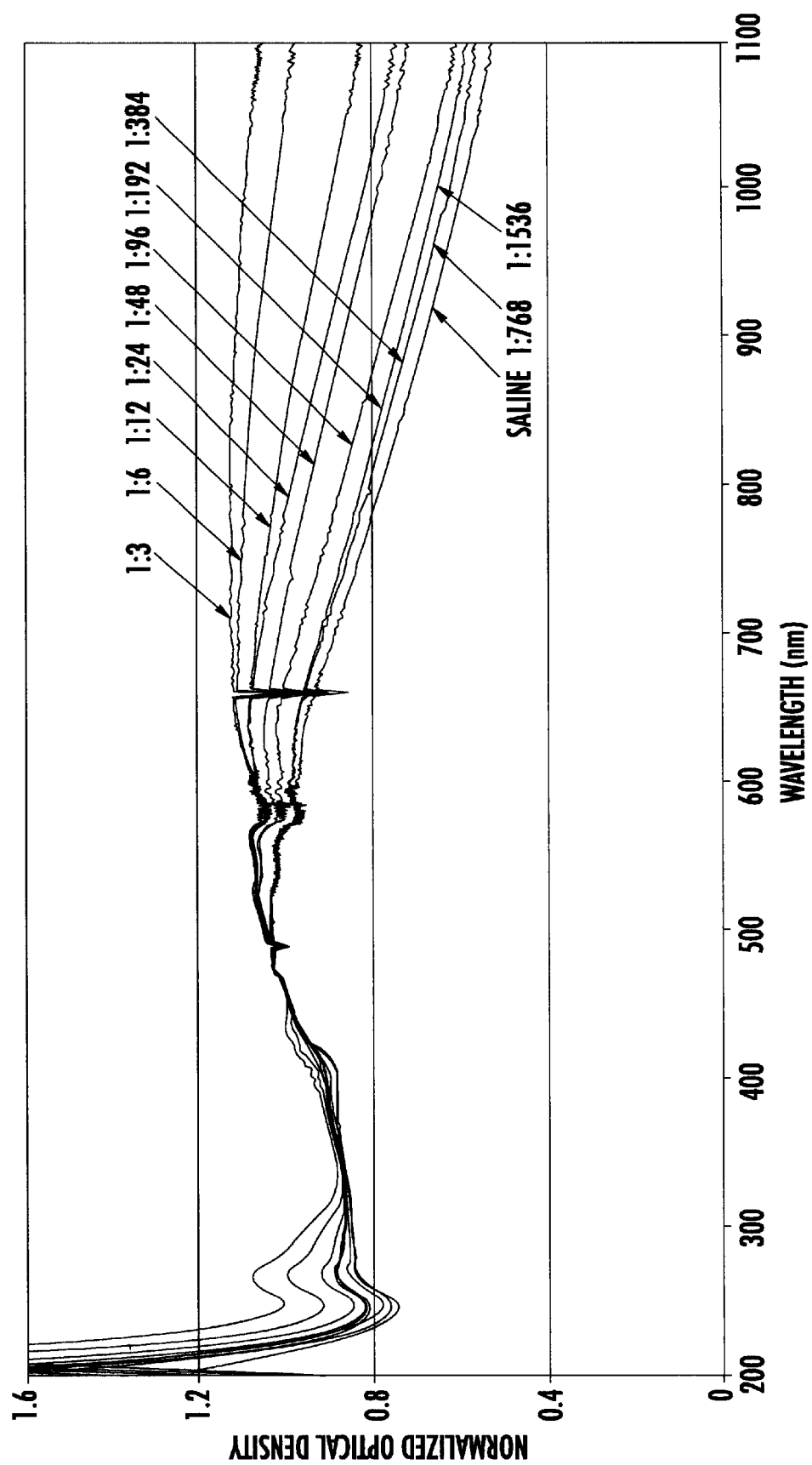
FIG. 4A plots normalized optical density spectra of group A reagent red blood cells in the presence of anti-A reagent at varying concentrations normalized relative to the OD at 460 nm. A general flattening of the spectra was observed at higher concentrations of anti-A.
Figure 4B:
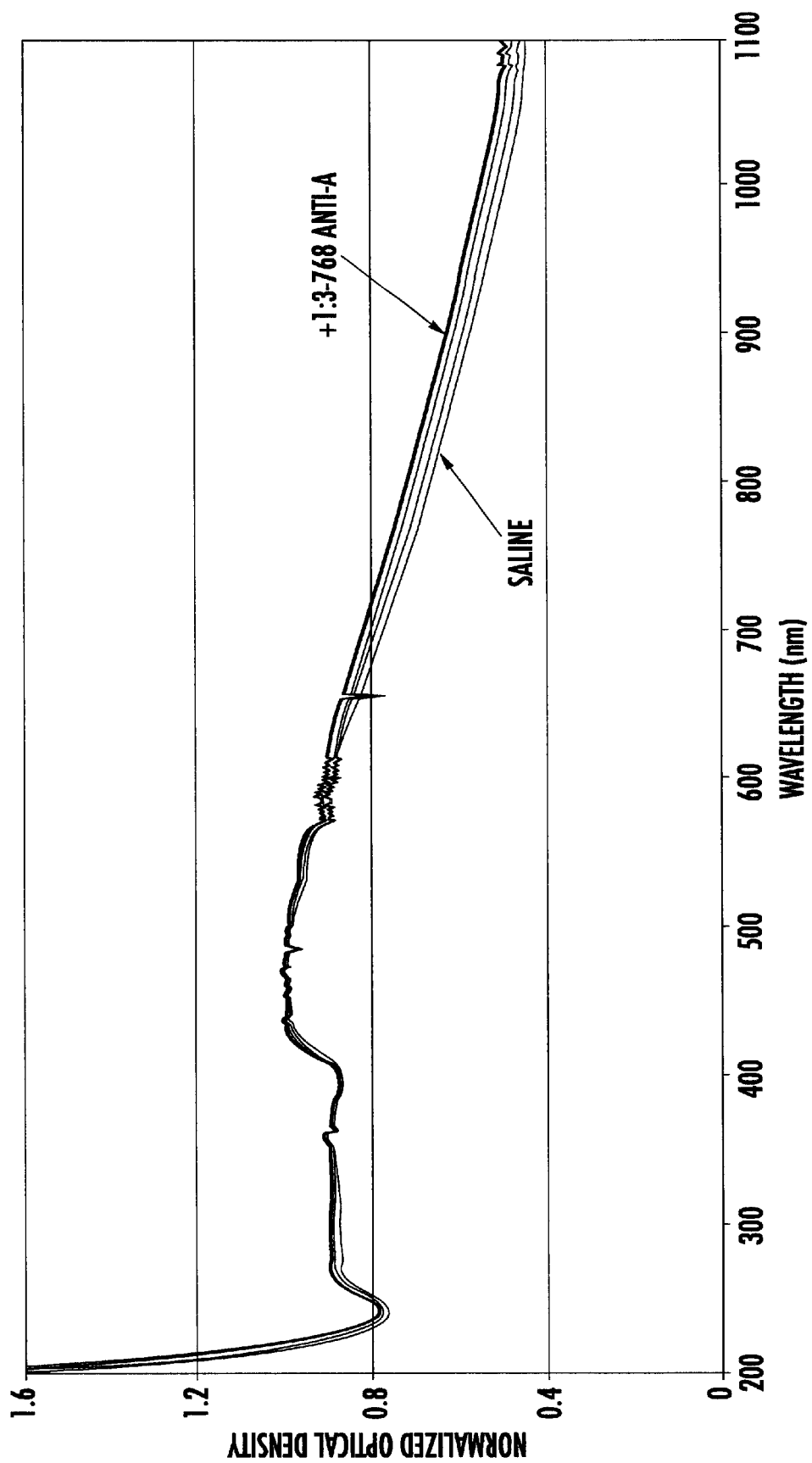
FIG. 4B plots normalized optical density spectra of group B reagent red blood cells in the presence of anti-A reagent at varying concentrations normalized relative to the OD at 460 nm. There was little change observed in the samples containing anti-A reagent as compared with the sample in saline.

To examine the sensitivity of the methodology, previously typed blood was exposed to varying dilutions of agglutinating antibody and the AI was calculated (FIG. 4A). For blood type A in the presence of anti-A AIs uniformly decreased as the concentration of diluted antibody decreased (1:3–1:768) (Table 4a). In contrast, type B blood exposed to similar anti-A antibody, as expected, yielded no spectrally detectable agglutination (FIG. 4B) and very low AIs (−0.4 to −6). All indices for nonagglutinating reaction were well below the lowest value of 4 units or more for samples deemed by standard blood banking tests to give true agglutination reactions (Table 4b).

TABLE 4a

Sensitivity: Blood Type A vs. Anti-A

| Sample | Standardized Slope Slope/Saline Slope | Agglutination Index |
|---|---|---|
| 1:3 | 9.3 | 90.7 |
| 1:6 | 29.4 | 70.6 |
| 1:12 | 64.0 | 36.0 |
| 1:24 | 83.2 | 16.8 |
| 1:48 | 85.7 | 14.3 |
| 1:96 | 106.7 | −6.7 |
| 1:192 | 104.6 | −4.6 |
| 1:384 | 104.0 | −4.0 |
| 1:768 | 103.3 | −3.3 |

TABLE 4b

Sensitivity - Control: Blood Type B vs. Anti-A

| Sample | Standardized Slope Slope/Saline Slope | Agglutination Index |
|---|---|---|
| 1:3 | 102.6 | −2.6 |
| 1:6 | 101.0 | −1.0 |
| 1:12 | 101.8 | −1.8 |
| 1:24 | 101.5 | −1.5 |
| 1:48 | 103.1 | −3.1 |
| 1:96 | 106.6 | −6.6 |
| 1:192 | 105.1 | −5.1 |
| 1:384 | 103.1 | −3.1 |
| 1:768 | 100.4 | −0.4 |

Figure 5:
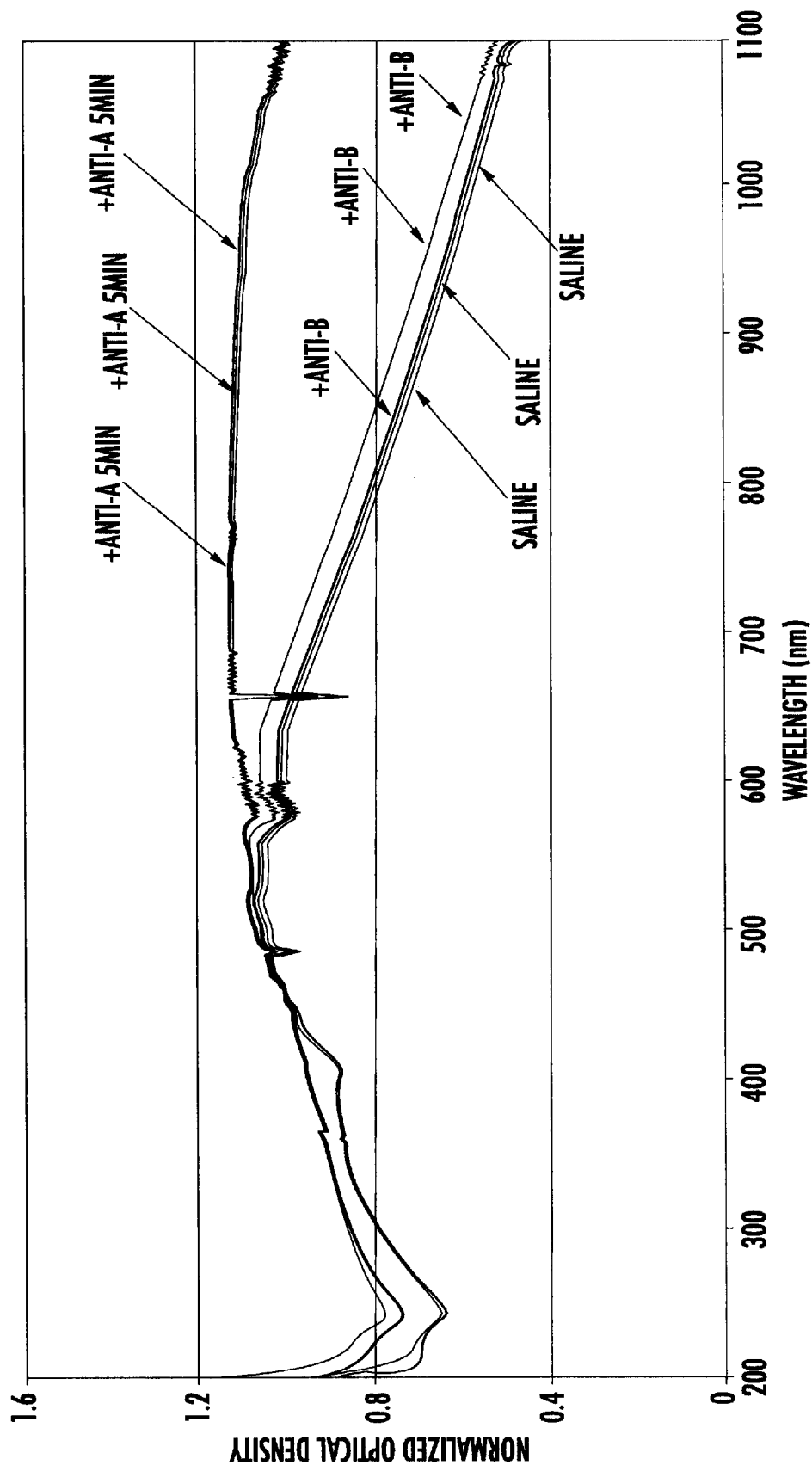
FIG. 5 plots three runs of group A type A red blood cells in the presence of anti-A and anti-B reagents normalized relative to the OD at 460 nm. All three runs overlay and yielded close agglutination indexes.

Reproducibility. The reliability of this procedure has been further examined in three ways. First, three separate analyses of a single blood type (A) with both anti-A and anti-B were performed, as can be seen in FIG. 5. The control and experimental (agglutination) spectra are almost identical. Examination of AIs reflects the high reproducibility of this approach (Table 5). Second, an additional set of three control samples of blood were analyzed, which were tested a total of 5 times each (Table 6). AIs obtained for each of these were very close in magnitude (<5 units), as evidenced by the low standard deviation ($\sigma<2$) and variance (±2). Third, blood type B was incubated with anti-A, and its optical density spectrum was monitored over 20 min. As expected, no reaction was apparent from the spectra, and this conclusion was corroborated by very low AIs (<2) (FIG. 2B).

TABLE 5

Reproducibility: Triplicate Analysis of Type A with Anti-A and Anti-B

| Sample | Antibody | Standardized Slope Slope/Saline Slope | Agglutination Index |
|---|---|---|---|
| 26 | Anti-A | 12.3 | 87.7 |
| 26 | Anti-B | 104.9 | −4.9 |
| 27 | Anti-A | 9.9 | 90.1 |
| 27 | Anti-B | 104.9 | −4.9 |
| 28 | Anti-A | 12.5 | 87.7 |
| 28 | Anti-B | 102.0 | −2.0 |

TABLE 6

Reproducibility: Replicate slopes of Red Blood Cells in Saline

| Sample | | Blood Type | Standardized Slope Slope/Saline Slope | Agglutination Index | Variance of Norm. Slopes |
|---|---|---|---|---|---|
| 29 | saline 1 | AB positive | 99.5 | 0.5 | 0.757 |
| | saline 2 | | 100 | 0.0 | |
| | saline 3 | | 99.7 | 0.3 | |
| | saline 4 | | 98.9 | 1.1 | |
| | saline 5 | | 97.8 | 2.2 | |
| 30 | saline 1 | A positive | 100 | 0.0 | 2.560 |
| | saline 2 | | 95.5 | 4.5 | |
| | saline 3 | | 97.4 | 2.6 | |
| | saline 4 | | 97.8 | 2.2 | |
| | saline 5 | | 97.8 | 2.2 | |
| 31 | saline 1 | O positive | 99.1 | 0.9 | 0.362 |
| | saline 2 | | 100 | 0.0 | |
| | saline 3 | | 100 | 0.0 | |
| | saline 4 | | 99.4 | 0.6 | |
| | saline 5 | | 98.6 | 1.4 | |

| Sample | Standard Deviation of Standardized Slopes | 95% Confidence Interval of Normal Slopes |
|---|---|---|
| I | 0.87 | +/−1.00 |
| II | 1.60 | +/−1.84 |
| III | 0.60 | +/−0.69 |

Figure 6:
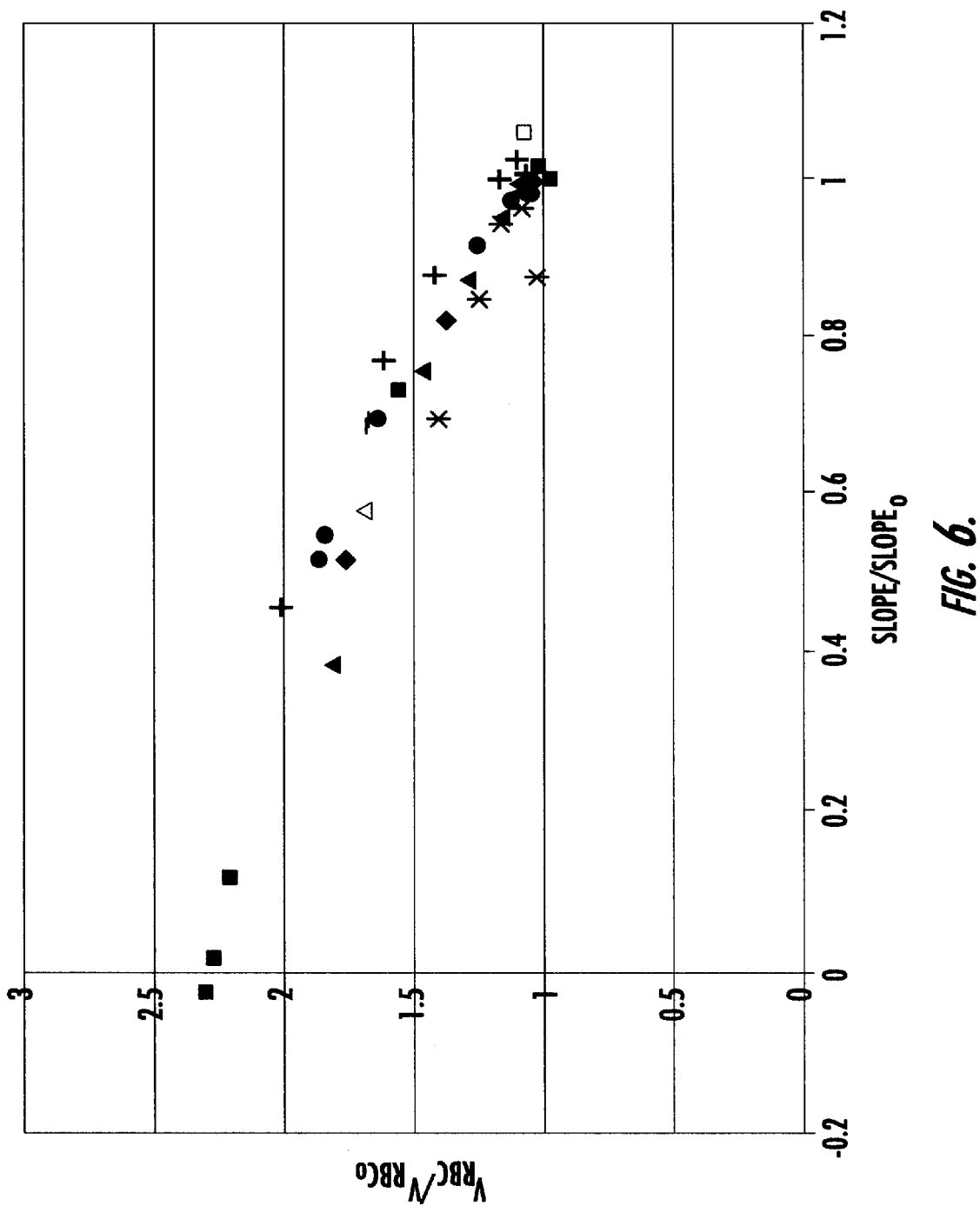
FIG. 6 plots the relative change in the size of red blood cells with a relative change in slope, illustrating an evident trend.

FIG. 6 shows an analysis of the relationship between slopes of the spectra (between 665 and 1000 nm) and calculated particle sizes of the red cells from respective spectra. Slopes of all the spectra were divided by the slope of the sample in saline. Volumes were calculated using an algorithm based on Mie scattering theory and the optical properties of erythrocytes. The software takes into account the refractive indices of the medium, the scattering by the red cells, and absorption components of the main blood components. Estimated average diameters of the red blood cells in solution are used to calculate average volumes, which were then divided by the volume obtained for the sample in saline. This was plotted versus the ratio of slopes, resulting in a scatter pattern. Eleven samples were analyzed comprising a broad range of samples examined in the experiments previously described. These samples showed a generally linear relationship between the ratio of slopes, which is used to calculate AI and the relative size or volume of the particles in solution. Clearly, as the ratio of slopes dropped, the average volume of the particles in solution (cell aggregates) increased. As expected, the AI correlated directly with estimated changes in cell agglutination due to antigen-antibody reaction.

DISCUSSION

A simple blood typing procedure for A,B,O and D based on multiwavelength uv/vis spectroscopy has been developed. It provides an objective and quantitative evaluation of the antibody-erythrocyte interaction that makes automation of this blood typing system possible. The speed and simplicity of the approach comes from the limited number of steps required for analysis. A dilution of blood is mixed with either saline or appropriate solutions of antibodies (anti-A, anti-B, anti-D), incubated for 1 min or longer and the full uv/vis spectrum is recorded on any rapid scan or diode array spectrophotometer. An objective evaluation of the degree of antibody-induced erythrocyte agglutination is calculated by comparing the normalized slopes of antibody-treated samples to the unperturbed blood sample in saline. The analysis can be accomplished by software that calculates the agglutination index (AI) directly from the spectrum using a set cutoff value to reliably indicate the blood type.

The evaluation of whole blood spectra shows significant changes throughout the uv/vis range upon addition of agglutinating antibodies. The wavelength range between 600 and 1000 nm is best suited for our present method, since only very weak absorption by the chromophores of blood components occurs within that range. This leaves forward-scattered light as a dominant contribution to the optical density. Since the transmission spectrum or optical density of a sample is composed of some combination of absorption and scattering (Brandolin et al., 1991), which ranges from 0 to 100% of each depending on the size of particles and presence or absence of absorbing species, the optical density of blood between 600–1000 nm is thus composed of only the forward-scattered light from cells or cell aggregates. This scattering in turn is a reflection of the size of the particles (i.e., red blood cells) and their state of agglutination. This relationship is described in detail by Mie Scattering Theory (Brandolin et al., 1991). The full solution of this theory (Kerker, 1969) as applied to blood has the potential of yielding a wealth of information such as the number of cells and their average diameters or volumes.

Herein relative measurements are used. Each blood sample is evaluated for agglutination in comparison to itself, and therefore the differences in the spectra are used to obtain the AI. Importantly, the resultant index increases with the degree of antibody-induced aggregation and is consistently small in the presence of nonagglutinating antibody. Furthermore, as shown in FIG. 6, the index can be related to the changes in particulate volume (agglutinated cells) brought on by antibody-induced agglutination. The calculated AI increases as the estimated relative particle volume (calculated from Mie Theory) increases and thus the AI can be shown to have a theoretical basis.

The AI correlates well with the degree of antibody-induced red cell aggregation. As would be expected from the number of antigenic sites, anti-A agglutinates type AB blood more strongly than anti-B blood. This is reflected in the magnitude of the AIs (Table 1a) calculated for several samples of blood type AB treated with antibody. Furthermore, the calculated index increases with time of antibody exposure to cells, which correlates very well with visual examination of agglutination reactions (Table 2). Increasing amounts of agglutinating antibody, which are known to cause stronger agglutination reactions, show increasing AIs. Importantly, AIs for blood in the presence of nonagglutinating antibodies show little to no change over these same extended time periods (FIG. 2B). Thus the index responds as expected and can be interpreted as reflecting the degree of agglutination.

Regardless of how one chooses to interpret the magnitude of the calculated AIs, it can clearly be used to establish a yes/no blood typing protocol. Nonagglutinating antibodies show very low AIs (<3.5), while agglutinating samples all show values of more than 17. Thus a cutoff value indicating no reaction could easily be established. To date in over 70 samples, there have been no false positives, and all normal ABO and normal D have given AIs of over 17 with only 1 min of incubation. Since larger agglutination values are obtained with extended time frames or increased agglutinating antibody concentrations, any questionable samples could be incubated for longer times or retested by an addition of more antibody. Those same treatments have little to no effect on samples of blood exposed to nonagglutinating antibodies and so provide a simple means of corroboration or rechecking of results. Initial trials with subsets of A (namely, $A_2$ and $A_2B$ types) show these to be easily identified as well (data not shown), while weak D types give signals that require the addition of enhancement agents and longer incubation times (data not shown).

Two other features of this blood typing system are of note. First, an example of the value of taking full wavelength spectra is seen in the ability of the test to detect hemolyzed samples. Lysis of erythrocytes leads to an increase in soluble hemoglobin and a concomitant change in the spectra. In particular, an easily detected peak is seen at 417 nm. Changes in this region can be used to identify and if desired quantify the degree of hemolysis. A second feature of the test is that rouleaux or non-antibody-induced association of erythrocytes is avoided by the significant dilution of blood prior to testing. The high sensitivity of the test allows for very low levels of blood cells (4000 cells/$\mu$l) to be used. False positives from rouleaux formation, which is typically seen only at concentrations of 10,000 cell/$\mu$l or more (Mollison, 1993), is thus avoided.

Also, the reproducibility of the present typing procedure is very high, as indicated by the low standard deviation and coefficients of variation. The large difference in AI between agglutinated and nonagglutinated samples coupled with the high reproducibility will make it easy to establish liberal cutoff values for agglutination and thus blood typing. The lack of false positives even with extended times of incubation or increased antibody concentration is extremely significant and speaks to the reliability of the method.

Importantly, as the specific uv/vis characteristics (both scattering and absorption) of the major components of blood become established, these can be used to extract more quantitative data on cell numbers and sizes, which Mie theory indicates is contained in the full wavelength spectra. At that time an AI based on actual sizes of aggregates instead of the relative changes described here will be made possible. Importantly, this will not require any reconfiguration of the test. A simple change of computer software will suffice.

Finally, while only a small portion of the information contained in the spectra has been used to develop a reliable blood typing technique, this blood analysis platform clearly offers a number of other exciting possibilities. The simplicity of the approach coupled with miniaturization of uv/vis instrumentation makes the present test highly mobile. This is believed to be of value for bedside situations, in emergencies, or for blood analysis in rural areas.

References

Anderson, N. M., Sekelj, P. "Light-Absorbing and Scattering Properties of Non-Haemolysed Blood," *Phys. Med. Biol.* 12(2), 173–84 (1967).

Beutler, E., Marshall, A. L., Coller, B. S., et al., *Williams Hematology*, 5$^{th}$ ed., McGraw-Hill (1995).

Brandolin, A., Garcia-Rubio, L. H., Provder, T., Kohler, M. E., and Kuo, C., "Latex Particle Size Distribution from Turbimetry Using Inversion Techniques, Experimental Validation," ACS Symposium on Hyphenated Techniques in Polymer Characterization, Chicago, August 22–27, No. 472 (1991), Chap. 2.

Britton, N. F., *Reaction Diffusion Equations and Their Applications to Biology*, Academic, N.Y. (1978).

Campbell, D., and White, J. R., *Polymer Characterization: Physical Techniques*, Chapman and Hall, London (1989).

Chang, S. H., "Modeling and Analysis of Fiber Optic Sensors," PhD Dissertation, Univ. South Florida (1996).

Chang, S. H., and Garcia-Rubio, L. H., "Modeling of Fiber Optic-Based Sensors," *Chemical, Biochemical, and Environmental Fiber Sensors V* 2068, 11 (1993).

Chang, S. H., and Garcia-Rubio, L. H., "Determination of pH with Acid-Base Indicators: Feasibility Analysis for Optical Fiber Probes," *Talanta*, to be published.

Chang, S. H., Druen, S. L., and Garcia-Rubio, L. H., "Modeling and Analysis of Fiber Optic pH Sensors: Effect of the Ionic Strength," *SPIE Proc.*, 2388 (1995).

Chang, S. H., Koumarioti, Y., and Garcia-Rubio, L. H., "Turbidimetric Analysis of SiO$_2$ Particles," *J. Coll. Interface Sci.*, to be published.

Chang, S. H., Byrne, R. H., and Garcia-Rubio, L. H., "Comparison of Behavior of Indicator Dyes in Solution and Immobilized in a Polymer Matrix for pH Measurements," *Anal. Chem.*, submitted.

Elicabe, G., and Garcia-Rubio, L. H., "Latex Particle Size Distribution from Turbimetry Using a Combination of Regularization Techniques and Generalized Cross Validation," *Adv. Chem. Series* 227, Chap. 6 (1990).

Gane, P., Vellayoudom, J., Mollocine, R., Breimer, M. E., et al. "Heterogeneity of Anti-A and Anti-B Monoclonal Reagents. Agglutination of Some Weak ABX Erythrocyte Variants and Recognition of Synthetic Oligosaccharide and Tissue Antigens. *Vox. Sang.* 53. 117–25 (1987).

Garcia-Rubio, L. H, "Averages from Turbimetry Measurements," *ACS Symp. Ser.* 332, 161 (1987).

Garcia-Rubio, L. H., "The Effect of Molecular Size on the Absorption Spectra of Macromolecules," *Macromol.* 20, 3070 (1987).

Garcia-Rubio, L. H., "Determination of the Absorption Coefficient of Proteins in the Presence of Protein Aggregates Using Turbimetry," *Chem. Eng. Comm.* 80, 193 (1989).

Garcia-Rubio, L. H., "Refractive Index Effects on the Absorption Spectra of Macromolecules," *Macromol.* 25, 2608 (1992).

Garcia-Rubio, L. H., "Multiangle-Multiwavelength Detection for Polymer Characterization," ACS *Symposium on Hyphenated Techniques in Polymer Characterization*, Chicago, Aug. 22–27, 1993.

Garcia-Rubio, L. H., and Ro, N., "Detailed Copolymer Characterization Using Ultraviolet Spectroscopy," *Can. J. Chem.* 63, 253 (1985).

Garcia-Rubio, L. H., Ro, N., and Patel, R. D., "UV Analysis of Benzoyl Peroxide Initiated Polymerizations and Copolymerizations," *Macromolecules* 17, 1998 (1984).

Garcia-Rubio, L. H., Rose, J., and Bacon, C., "Quantitative Characterization of Cryptosporidium Oocysts and Giardia Cysts Using UV-vis Spectroscopy," unpublished.

Golub, G. H., Heath, M., and Wahba, G., "Generalized Cross Validation as a Method for Choosing a Good Ridge Parameter," *Technometrics* 21, 215 (1979).

Horecker, B. L., "The Absorption Spectra of Hemoglobin and its Derivatives in the Visible and Near Infrared Regions," *J. Biol. Chem.* 148, 173–83 (1943).

Horecker, B. L., Brackett, F. S., "A Rapid Spectrophotometric Method for the Determination of Methemoglobin and Carbonylhemoglobin in Blood," *J Biol. Chem.* 152, 669–77 (1944).

Ishimaru, A., *Wave Propagation and Scattering in Random Media*, Vols. I and II, Academic, N.Y. (1978).

Kerker, M., Ed., *Electromagnetic Waves*, Pergamon, N.Y. (1969). Kortum, G., Reflectance Spectroscopy, Springer Verlag, Berlin-Heidelberg (1969).

Marquez, E., Bhethanabotla, V. R., and Garcia-Rubio, L. H., "Conformation Effects on the Absorption Spectra of Macromolecules," *Macromol.* 26, 479 (1993).

Melik, D. H., and Fogler, H. S., "Turbidimetric Determination of Particle Size Distributions of Colloidal Systems," *J. Coll. Interface Sci.* 92, 161 (1983).

Mollison, P. L., Engelfriet, C. P., Contreras, M. *Blood Transfusion in Clinical Medicine,* 9$_{th}$ ed., Blackwell Scientific Publications (1993).

Muller, A., Garrerca, M., Herbert, M. "Groupamatic System: Overview, History and Development and Evaluation of Use," *Vox Sang* 40, 201–13 (1981).

Olympus PK7200 Technical Manual, Osaka, 1993.

Ross, K. F. A., and Billing, E. J., "The Water and Solid Content of Living Bacterial Spores and Vegetative Cells as Indicated by Refractive Index Measurements," *Gen. Microbiol.* 16,418 (1957).

Rousseau, D. L., Ed., *Optical Techniques in Biological Research*, Academic, New York (1984).

Tarantola, A., *Inverse Problem Theory*, Elsevier, Amsterdam (1987). Thormälen, I., Straub, J., and Grigull, U., *J. Phys. Chem. Ref Data* 14(4), 933 (1985).

Towmey, S., *Introduction to the Mathematics of Inversion in Remote Sensing and Indirect Measurements*, Elsevier, New York (1979).

van de Hulst, H. C., *Light Scattering by Small Particles*, Wiley, N.Y. (1957).

Walker, R. H., Hope, P. A., Judd, W. J., et al. Technical Manual, 10$^{th}$ ed., Arlington, Va., American Association of Blood Banks (1990).

Wolf, E., and Born, M., *Principles of Optics*, Macmillan, N.Y. (1964).

Zollars, R. L., *J. Coll. Interface Sci.* 74, 163 (1980).

It may be appreciated by one skilled in the art that additional embodiments may be contemplated, including systems and methods for characterizing other bodily fluids and their constituents, such as, but not limited to, saliva and spinal fluid. In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A method for determining a type of a blood sample comprising the steps of:

collecting a reference optical density spectrum of a first subsample of a blood sample over a predetermined wavelength range generally in the ultraviolet-visible portion of the electromagnetic spectrum;

mixing a second subsample of the blood sample with an antibody corresponding to a known blood type;

collecting an antibody-treated optical density spectrum of the antibody-blood sample mixture over the predetermined wavelength range; and calculating a numerical indicator of agglutination by:

calculating a first slope of the reference optical density spectrum and a second slope of the antibody-treated optical density spectrum over at least a portion of the predetermined wavelength range; and dividing the first slope by the second slope to yield a numerical indicator of agglutination;

determine the blood type by comparing the numerical indicator of agglutination to a predetermined empirical value.

* * * * *